(12) United States Patent
Yang et al.

(10) Patent No.: US 9,613,260 B2
(45) Date of Patent: *Apr. 4, 2017

(54) APPARATUS AND METHOD FOR CALCULATING ENERGY CONSUMPTION BASED ON THREE-DIMENSIONAL MOTION TRACKING

(71) Applicant: Samsung Electronics Co., Ltd, Gyeonggi-do (KR)

(72) Inventors: Jun-Mo Yang, Suwon-si (KR); Giu-Yeol Kim, Suwon-si (KR); Dong-Yun Shin, Yongin-si (KR); Du-Seok Kim, Yongin-si (KR)

(73) Assignee: SAMSUNG ELECTRONICS CO., LTD, Suwon-si, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,946

(22) Filed: Jun. 15, 2015

(65) Prior Publication Data
US 2015/0278587 A1 Oct. 1, 2015

Related U.S. Application Data

(63) Continuation of application No. 13/624,777, filed on Sep. 21, 2012, now Pat. No. 9,076,226.

(30) Foreign Application Priority Data

Sep. 21, 2011 (KR) .................. 10-2011-0095057

(51) Int. Cl.
*G06K 9/00* (2006.01)
*A61B 5/00* (2006.01)
(Continued)

(52) U.S. Cl.
CPC ........ *G06K 9/00342* (2013.01); *A61B 5/0002* (2013.01); *A61B 5/0059* (2013.01);
(Continued)

(58) Field of Classification Search
CPC ........ A61B 2560/0475; A61B 2576/00; A61B 5/0002; A61B 5/0059; A61B 5/1072;
(Continued)

(56) References Cited

U.S. PATENT DOCUMENTS

| 2008/0139307 A1 | 6/2008 | Ueshima et al. |
| 2011/0054870 A1 | 3/2011 | Dariush et al. |

(Continued)

FOREIGN PATENT DOCUMENTS

| CN | 101090755 A | 12/2007 |
| JP | 2003-33337 | 2/2003 |

(Continued)

OTHER PUBLICATIONS

Extended European Search Report dated Feb. 4, 2013 in connection with European Patent Application No. 12185265.1; 7 pages.
(Continued)

*Primary Examiner* — Nirav G Patel

(57) ABSTRACT

An apparatus and method calculate an energy consumption based on 3D motion tracking. The method includes setting at least one specific portion of an analysis target as a reference point, analyzing the reference point before and after the lapse of a predetermined time, and determining an energy consumption of the analysis target on the basis of the analyzed reference point.

20 Claims, 7 Drawing Sheets

(51) Int. Cl.
*G06T 7/20* (2017.01)
*A61B 5/11* (2006.01)
*A61B 5/107* (2006.01)

(52) U.S. Cl.
CPC .......... *A61B 5/1072* (2013.01); *A61B 5/1073* (2013.01); *A61B 5/1079* (2013.01); *A61B 5/1118* (2013.01); *A61B 5/1121* (2013.01); *A61B 5/1128* (2013.01); *A61B 5/4528* (2013.01); *A61B 5/4866* (2013.01); *G06T 7/2033* (2013.01); *G06T 7/2086* (2013.01); *A61B 2560/0475* (2013.01); *A61B 2576/00* (2013.01); *G06T 2207/10028* (2013.01); *G06T 2207/30196* (2013.01)

(58) Field of Classification Search
CPC ... A61B 5/1073; A61B 5/1079; A61B 5/1118; A61B 5/1121; A61B 5/1128; A61B 5/4528; A61B 5/4866; G06K 9/00342; G06T 2207/10028; G06T 2207/30196; G06T 7/2033; G06T 7/2086
See application file for complete search history.

(56) References Cited

U.S. PATENT DOCUMENTS

| 2011/0288379 A1 | 11/2011 | Wu |
| 2011/0306468 A1 | 12/2011 | Wilson et al. |
| 2013/0268205 A1 | 10/2013 | Aragones et al. |

FOREIGN PATENT DOCUMENTS

| JP | 2005-1925968 | 7/2005 |
| WO | WO 2009015552 A | 2/2009 |

OTHER PUBLICATIONS

Text of First Office Action dated Feb. 27, 2015 in connection with Chinese Patent Application No. 2012103570559; 17 pages.

Communication pursuant to Article 94(3) EPC date Apr. 24, 2015 in connection with European Patent Application No. 1285265; 3 pages.

Shotton, et al.; "Real-Time Human Pose Recognition in Parts from Single Depth Images"; IEEE-CPVR; Jun. 20, 2011; 8 pages.

000# APPARATUS AND METHOD FOR CALCULATING ENERGY CONSUMPTION BASED ON THREE-DIMENSIONAL MOTION TRACKING

CROSS-REFERENCE TO RELATED APPLICATION(S) AND CLAIM OF PRIORITY

The present application is a continuation of U.S. patent application Ser. No. 13/624,777 which is related to and claims the benefit under 35 U.S.C. §119(a) to a Korean Patent Application filed in the Korean Intellectual Property Office on Sep. 21, 2011 and assigned Serial No. 10-2011-0095057, the entire disclosure of which both are hereby fully incorporated by reference.

TECHNICAL FIELD OF THE INVENTION

The present disclosure relates generally to an apparatus and method for calculating an energy consumption.

BACKGROUND OF THE INVENTION

Recently, a method of tracking a motion of a user by near infrared rays (NIR), digital cameras, web-cams, and optical devices has become in common use. For example, the method is used as a new interaction method for a console game.

Conventional methods of analyzing the calorie consumption of a user in motion may be classified into two types. The first method is to use a spirometer and a gas analyzer to measure and analyze an oxygen consumption and a carbon dioxide emission of a user during the breathing in motion. The second method is to input a predetermined calorie consumption into an apparatus or software and provide calorie information to a user according to the lapse of a predetermined time or a program process time.

However, because the first method measures a calorie consumption of a user with an expensive equipment (e.g., a spirometer or a gas analyzer) worn by the user, it may be difficult to apply to actual motion.

Also, because the second method calculates a calorie consumption of a user according to the lapse of a program process time, it may fail to reflect an actual motion quantity of the user.

SUMMARY OF THE INVENTION

To address the above-discussed deficiencies of the prior art, it is a primary object to provide at least the advantages below. Accordingly, an object of the present disclosure is to provide an apparatus and method for calculating an energy consumption based on 3D motion tracking, which can calculate a calorie consumption reflecting an actual motion quantity of a user in a noncontact manner.

Another object of the present disclosure is to track a 3D motion of a user by computer vision technology to analyze a motion quantity of each body region and calculate an accurate calorie consumption.

In accordance with an embodiment, a method for calculating an energy consumption based on three-dimensional (3D) motion tracking is provided. The method includes selecting at least one specific portion of an analysis target as a reference point, and analyzing the reference point before and after a lapse of a predetermined time. The method also includes determining an energy consumption of the analysis target on the basis of the analyzed reference point.

In accordance with another embodiment, an apparatus for calculating an energy consumption based on three-dimensional (3D) motion tracking is provided. The apparatus includes a recognition/detection module configured to select at least one specific portion of an analysis target as a reference point, and analyze the reference point before and after a lapse of a predetermined time. The apparatus also includes a calorie calculating unit configured to determine an energy consumption of the analysis target on the basis of the analyzed reference point.

In accordance with yet another embodiment, a system for calculating an energy consumption based on three-dimensional (3D) motion tracking is provided. The system includes a recognition/detection module configured to select at least one specific portion of an analysis target as a reference point, and analyze the reference point before and after a lapse of a predetermined time. The system also includes a calorie calculating unit configured to determine an energy consumption of the analysis target on the basis of the analyzed reference point. The system further includes a 3D optic module configured to recognize the analysis target in a 3D manner.

Before undertaking the DETAILED DESCRIPTION OF THE INVENTION below, it may be advantageous to set forth definitions of certain words and phrases used throughout this patent document: the terms "include" and "comprise," as well as derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

Figure 1A:
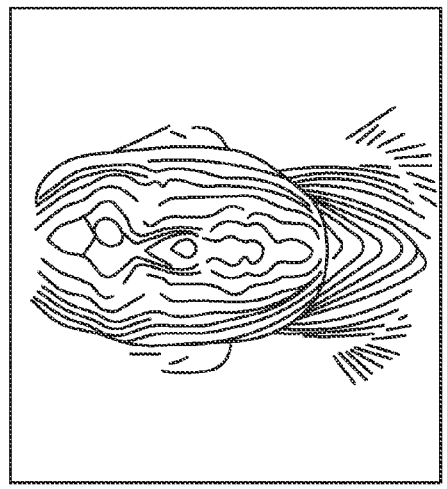
FIG. 1A is a diagram illustrating a method of structured light coding for 3D depth extraction which may be used in the present disclosure.

FIGS. 1A through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged apparatus.

The present disclosure relates to an apparatus and method for calculating an energy consumption based on three-dimensional (3D) motion tracking.

Exemplary embodiments of the present disclosure will be described herein below with reference to the accompanying drawings. In the following description, detailed descriptions of well-known functions or configurations will be omitted since they would unnecessarily obscure the subject matters of the present disclosure. Also, like reference numerals denote like elements throughout the drawings.

Figure 1B:
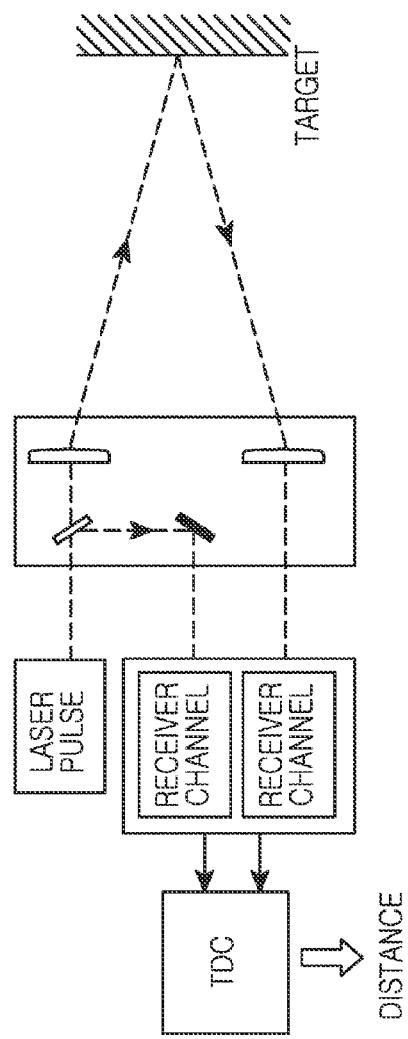
FIG. 1B is a structure diagram illustrating a technology of a time of flight for 3D depth extraction which may be used in the present disclosure.

FIG. 1A is a diagram illustrating a method of structured light coding for 3D depth extraction which may be used in the present disclosure. FIG. 1B is a diagram illustrating a technology of a time of flight for 3D depth extraction which ma be used in the present disclosure. FIG. 1A is a diagram acquired from the internet site (Uniform Resource Location, URL) for illustrating a dynamic structured light acquisition for facial scans using a set of lines projected onto a face to generate a 3D surface from a distance. URL is http://www.swri.org/4org/d14/ElectroSys/biometrics/current.htm.

FIG. 1B is a structure diagram illustrating a principle of a pulsed time-of-flight laser rangefinder which is disclosed in "Chapter 2. Pulsed time-of-flight laser rangefinding" of Academic Dissertation "Integrated electronic and optoelectronic circuits and devices for pulsed time-of-flight laser rangefinding" by Pasi Palojärvi (Faculty of Technology, Department of Electrical and Information Engineering, University of Oulu, 2003). Here, a pulsed time-of-flight laser rangefinding device consists of a laser pulse transmitter, the optics, two receiver channels and a time-to-digital converter (TDC). The laser pulse transmitter emits a short optical pulse to an optically visible target and the transmission event is defined optically by detecting a fraction of the pulse from the drive signal of the laser diode. The start pulse is then processed in a receiver channel, which generates a logic-level start pulse for a TDC. The optical pulse reflected from the target and collected by the photodetector of the stop receiver channel is processed and a logic-level stop pulse is generated for the TDC. The TDC uses its time base to convert the time interval to a digital word which represents the distance from the target.

A method using structured light coding for 3D depth extraction is one of the infrared-based 3D extraction methods, which projects patterned infrared rays and performs infrared photographing and decoding. Specifically, in a method using a depth image, an extraction target is projected by patterned infrared rays, and infrared photographing is performed to extract the depth of an analysis target. That is, an analysis target may be extracted not two-dimensionally but three-dimensionally to extract the height or depth thereof. Referring to FIG. 1A, a human face is an extraction target, and a method using structured light coding for 3D depth extraction which may be used in the present disclosure may be used to provide 3D extraction of the curve of a forehead, the depth of an eye, the height of a nose, and the protrusion around a mouth. Referring to FIG. 1B, a method using a time of flight is one of the infrared-based 3D extraction methods, which perform 3D extraction using the reflection time of infrared rays. Specifically, infrared rays are irradiated onto an analysis target, and a 3D shape is extracted using the reflection time of the infrared rays. That is, as the reflection time of the infrared rays increases, the analysis target is determined to be located more distantly (deeply). In contrast, as the reflection time of the infrared rays decreases, the analysis target is determined to be located more closely.

Figure 2:
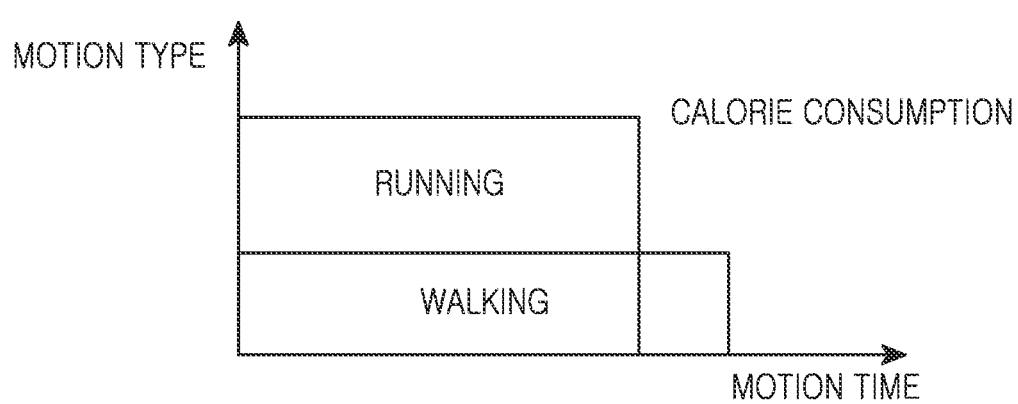
FIG. 2 is a graph illustrating a fixed table-based calorie consumption calculating method according to the related art.
Figure 3:
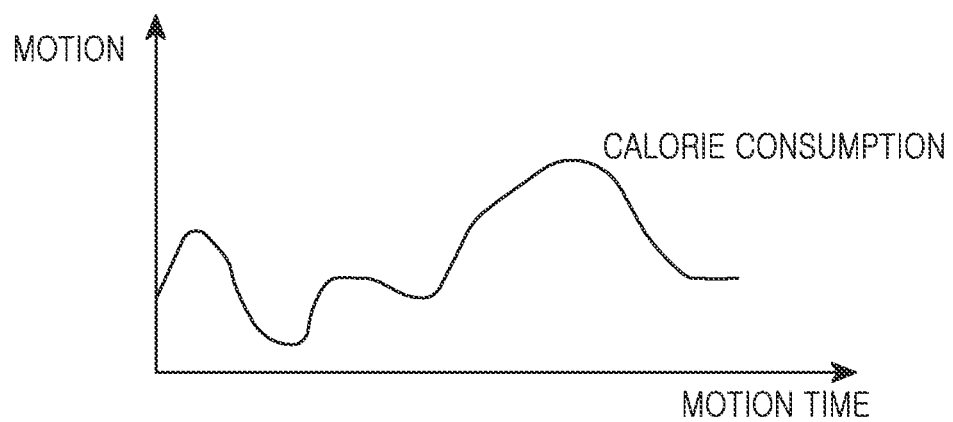
FIG. 3 is a graph illustrating a real-time calorie consumption calculating method according to the present disclosure.

FIG. 2 is a graph illustrating a fixed table-based calorie consumption calculating method according to the related art. FIG. 3 is a graph illustrating a real-time calorie consumption calculating method according to the present disclosure. Referring to FIG. 2, a fixed table-based calorie consumption calculating method calculates a calorie consumption of a user according to the lapse of a program process time, which may fail to reflect an actual motion quantity of the user. That is, the fixed table-based calorie consumption calculating method may fail to accurately estimate an actual motion quantity of the user. Thus, the fixed table-based calorie consumption calculating method may provide the fixed result regardless of the actual motion quantity of the user. For example, referring to FIG. 2, the X axis represents a motion time, the Y axis represents a motion type, and the area inside the rectangles represents a calorie consumption. Because running consumes more calorie than walking, the Y-axis value for running is greater than the Y-axis value for walking. As shown in FIG. 2, without substantial consideration of the Y-axis values (motion type) for walking and running according to the lapse of a motion time, a uniform value is substituted to calculate a calorie consumption of an analysis target. Thus, it may be difficult to calculate a substantial calorie consumption of the analysis target.

FIG. 3 illustrates a real-time calorie consumption calculating method according to the present disclosure, which reflects an actual motion quantity of a user. Referring to FIG. 3, the X axis represents a motion time, the Y axis represents a motion type, and an area under the curve represents a calorie consumption. As shown in FIG. 3, without consideration of a specific motion type according to the lapse of a motion time, a substantial motion quantity of each motion type is substituted to calculate a calorie consumption. Thus, unlike the conventional method of calculating a calorie consumption by substituting a uniform value, the real-time calorie consumption calculating method according to the present disclosure can calculate an accurate calorie consumption by substituting a real-time varying motion quantity.

Figure 4:
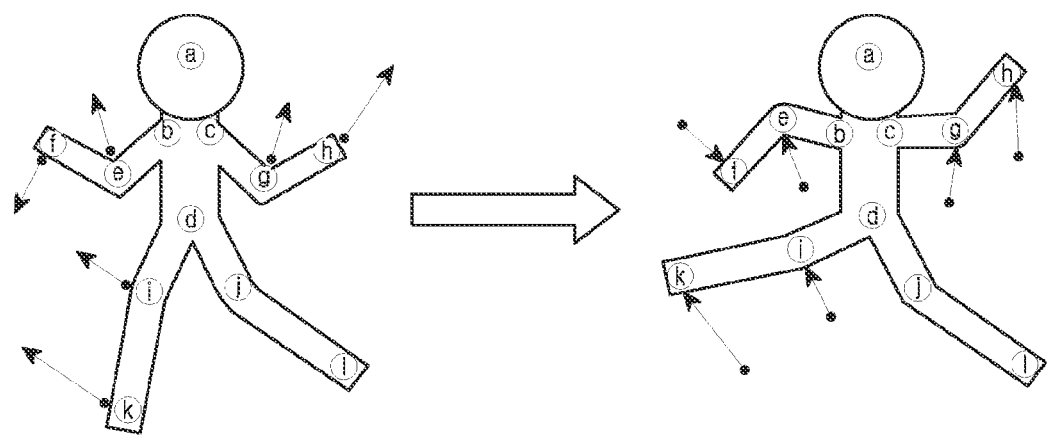
FIG. 4 is a diagram illustrating an embodiment of tracking a motion change of an analysis target between frames according to the present disclosure.

FIG. 4 is a diagram illustrating an embodiment of tracking a motion change of an analysis target between frames according to the present disclosure. A calorie consumption is calculated by analyzing a user skeleton on a 3D screen inputted on a frame-by-frame basis through a computer vision. Specifically, a 3D skeleton provides a X/Y/Z-axis space vector of a 3D position of each body region of an analysis target, and it may be used to analyze a motion of the analysis target between frames. That is, at least one specific portion of the analysis target is selected and set as a reference point. Then, the reference point after the lapse of a predetermined time with respect to the reference point before the motion of the analysis target is analyzed to analyze an energy consumption of the analysis target.

Specifically, a plurality of reference points are set at each body region as illustrated in FIG. 4. For example, a plurality of reference points are set at the joints of each body region such as the arms, legs, head, and body. In the embodiment shown in FIG. 4, reference points are set at the wrists (f, h), elbows (e, g), and shoulders (b, c) in the arms, at the ankles (k, l) and knees (i, j) in the legs, and at the pelvis (d) in the body. Also, a reference point is set at the center of the head (a) to analyze a motion of the head. Each reference point may be the best point for measurement of a motion of each body portion. Reference points may also be set at other body portions (e.g., a finger, a toe, and the center of the body) than those illustrated in FIG. 4.

Thereafter, each reference point before the motion of the analysis target and each reference point after the lapse of a predetermined time are compared and analyzed by a 3D vector. As described above, the 3D vector comparing and analyzing method sets the reference point as the origin in a 3D space represented by X, Y and Z axes, and represents the reference point of the analysis target after the motion in the 3D space, to determine a substantial moving distance and speed thereof. Thus, the analysis target may be analyzed to analyze the speed and distance information of the analysis target.

Figure 5:
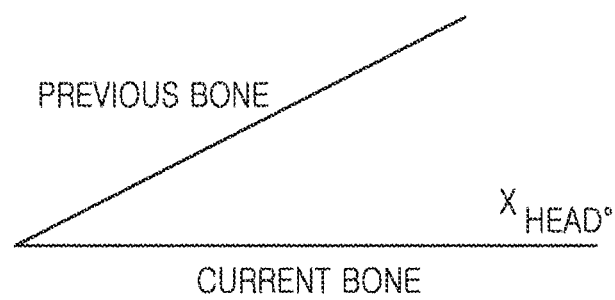
FIG. 5 is a diagram illustrating an embodiment of measuring a motion quantity of a body region based on a moving angle according to the present disclosure.

FIG. 5 is a diagram illustrating an embodiment of measuring a motion quantity of a body region based on a moving angle according to the present disclosure. For the embodiment described with respect to FIG. 5, it is assumed that a motion quantity of a head of an analysis target is measured. As described above, a reference point of the head is set at the center of the head. The reference point of the head of the analysis target before the motion is measured by computer vision technology, and the reference point after the lapse of a predetermined time is measured in the same manner. Thereafter, the reference point is analyzed by a space vector of X/Y/Z axes to measure the moving angle and distance thereof. FIG. 5 illustrates an example of measurement of the moving angle. As illustrated in FIG. 5, the position before the motion of the head and the portion after the motion of the head may be measured to measure the moving angle of the head. Although FIG. 5 illustrates an embodiment of the moving angle of the head, it will be understood that the moving angles of other body regions such as the arm, the leg, and the body may also be measured in the same manner.

Table 1 illustrates the factor of each body region depending on the weight and height of a human. With reference to Table 1, according to a weight (m) and a height (v), the volume of each body region (i) of a human may be calculated by Equation (1):

$$m_i = B_0 + B_1 m + B_2 v \quad \text{[Eqn. 1]}$$

In Equation (1), $m_i$ denotes the volume of each body region of a human, $B_0$, $B_1$ and $B_2$ are experimental values, m denotes the weight of the human, and v denotes the height of the human.

For example, with reference to Table 1, the volume of a leg of the human may be calculated by substituting the values of $B_0$, $B_1$ and $B_2$ in Equation (1) [Volume of leg of human=−0.829+0.0077×Weight+0.0073×Height]. The volume of a hand of the human may be calculated in the same manner [Volume of hand of human=−0.1165+0.0036× Weight+0.00175×Height].

TABLE 1

| Segment name | $B_0$ [kg] | $B_1$ | $B_2$ [kg/cm] |
| --- | --- | --- | --- |
| Head + neck | 1.296 | 0.0171 | 0.0143 |
| Hand | −0.1165 | 0.0036 | 0.00175 |
| Forearm | 0.3185 | 0.01445 | −0.00114 |
| Upperarm | 0.25 | 0.03012 | −0.0027 |
| Leg | −0.829 | 0.0077 | 0.0073 |
| Shank | −1.592 | 0.03616 | 0.0121 |
| Thigh | −2.649 | 0.1463 | 0.0137 |
| Upper part of the trunk | 8.2144 | 0.1862 | −0.0584 |
| Middle part of the trunk | 7.181 | 0.2234 | −0.0663 |
| Lower part of the trunk | −7.498 | 0.0976 | 0.04896 |

Thereafter, a motion quantity $m_t$ may also be calculated by Equation (2):

$$m_t = \sum_{i=1}^{11} (X_i^o \times (B_0 + B_1 W_t + B_2 V)\alpha) \quad \text{[Eqn. 2]}$$

In Equation (2), α denotes a corrected value of each factor, which may be obtained through actual measurement. $X_i$ denotes the moving angle of each body region described with reference to FIG. 5. The reason for calculation of the sum of values for i values from 1 to 11 is that there are 11 lines connecting 12 reference points as illustrated in FIG. 4. Thus, when N reference points are set, i values from 1 to N−1 are substituted.

Thereafter, a calorie consumption of the human may be calculated by Equation (3):

$$f(c) = \sum_{t=1}^{T} (0.0175 \times m_t \times W_t \times \beta HR_t) \quad \text{[Eqn. 3]}$$

In Equation (3), $W_t$ denotes the weight of the human, and βHRt denotes a corrected value of each factor, which may be obtained through actual measurement. t values from 1 to T (i.e., the total motion time) are substituted, and the respective result values are summed to calculate the calorie consumption.

Figure 6:
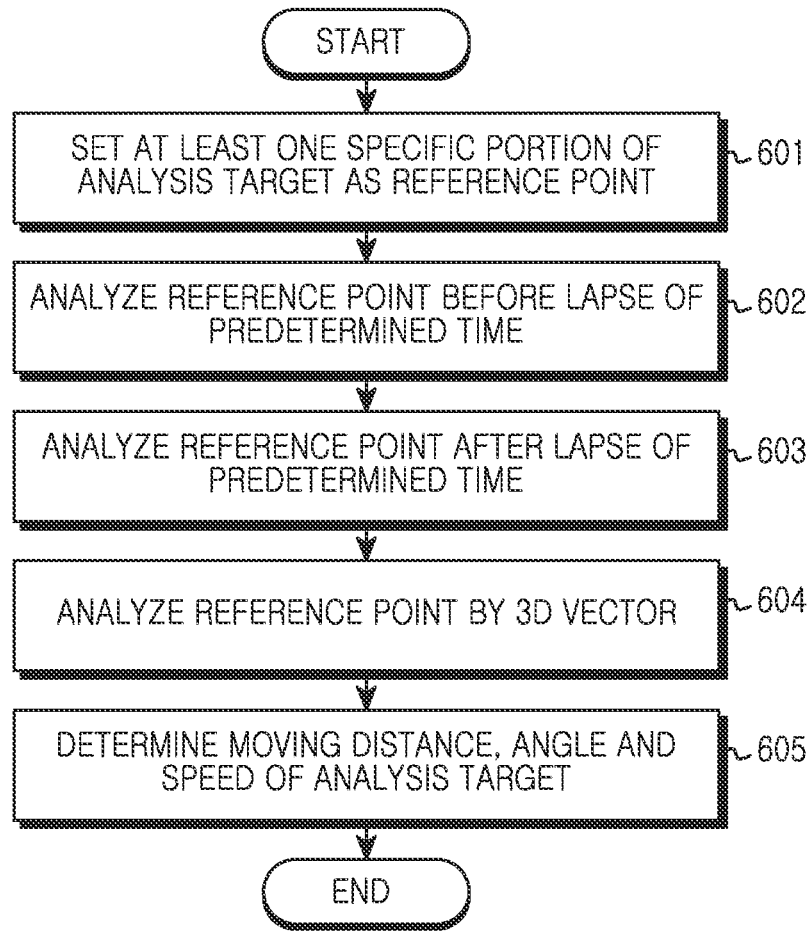
FIG. 6 is a flow diagram illustrating a method for calculating an energy consumption based on 3D motion tracking according to an embodiment of the present disclosure.

FIG. 6 is a flow diagram illustrating a method for calculating an energy consumption based on 3D motion tracking according to an embodiment of the present disclosure. Referring to FIG. 6, in block 601, the method sets at least one specific portion of an analysis target as a reference point. The specific portion may include at least one joint of a body region of the analysis target. This is because it is efficient to detect a motion of the joint in order to calculate an actual calorie consumption of the analysis target.

Thereafter, in block 602, the method analyzes the reference point before the lapse of a time predetermined by a user. Specifically, the method may use 3D optical module technology to analyze a skeleton of the analysis target on a 3D screen inputted on a frame-by-frame basis, to calculate a calorie consumption. Thereafter, in block 603, the method analyzes the reference point after the lapse of a predetermined time.

Thereafter, in block 604, the method analyzes the reference point by a 3D space vector. The method uses a 3D vector to compare and analyze the reference point before the motion of the analysis target and the reference point after the lapse of a predetermined time. Specifically, the method sets the reference point as the origin in a 3D space represented by X, Y and Z axes, and represents and analyzes the reference point of the analysis target after the motion in the 3D space. Thereafter, in block 605, the method determines the moving distance, angle and speed of the analysis target.

The method described above in relation with FIG. 6 under of the present invention may be provided as one or more instructions in one or more software modules stored in an electronic device such as, for example, a smart phone and a mobile telecommunication terminal.

Figure 7:
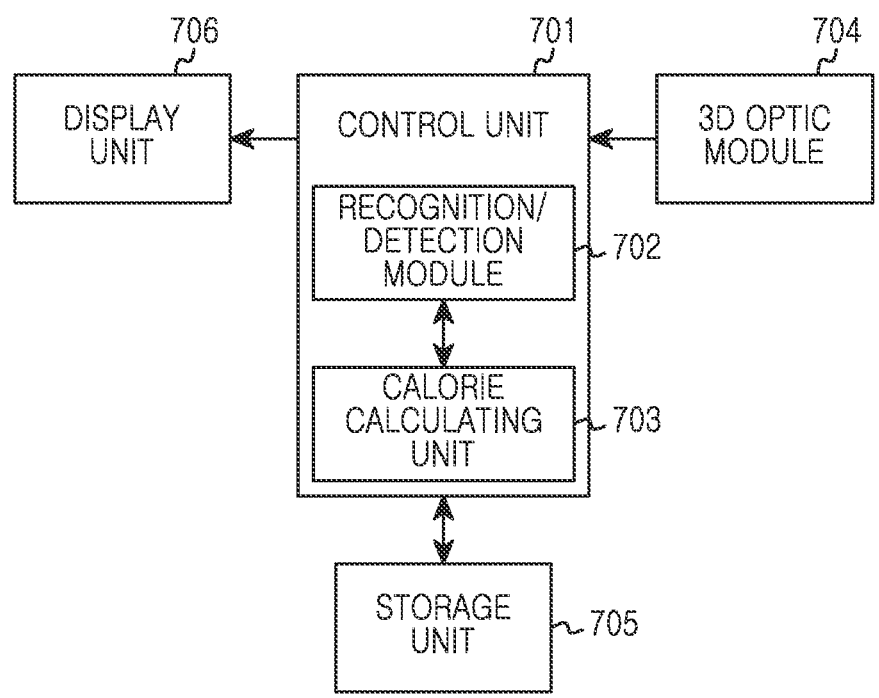
FIG. 7 is a block diagram illustrating an apparatus for calculating an energy consumption based on 3D motion tracking according to an embodiment of the present disclosure.

FIG. 7 is a block diagram illustrating an apparatus for calculating an energy consumption based on 3D motion tracking according to an embodiment of the present disclosure. Referring to FIG. 7, the apparatus may include a control unit 701, a recognition/detection module 702, a calorie calculating unit 703, a 3D optic module 704, a storage unit 705, and a display unit 706.

The control unit 701 controls an overall operation of the energy consumption calculating apparatus. The control unit 701 may include the recognition/detection module 702 and the calorie calculating unit 703.

The recognition/detection module 702 recognizes an analysis target on a 3D screen and tracts a motion of a body. For example, the recognition/detection module 702 selects at least one specific portion of an analysis target, sets the specific portion as a reference point, and analyzes the reference point after the lapse of a predetermined time with respect to the reference point before the motion of the analysis target.

The calorie calculating unit 703 tracks a motion of each body region to calculate a real-time calorie consumption. For example, the calorie calculating unit 703 analyzes the reference point to analyze an energy consumption of the analysis target, and compares and analyzes the reference point before the motion of the analysis target and the reference point after the lapse of a predetermined time by a 3D vector. Also, the calorie calculating unit 703 analyzes the reference point to analyze information about the moving speed and distance of the analysis target, and uses 3D optic module technology. The 3D optic module 704 may be a computer vision module that recognizes an object in a 3D manner.

The storage unit 705 may include a program storing unit configured to store a program for controlling an operation of the energy consumption calculating apparatus, and a data storing unit configured to store data generated during program execution. For example, the storage unit 705 stores calorie accumulation information calculated in real time.

Under the control of the control unit 710, the display unit 706 displays the state information, menu screen, and story information of the energy consumption calculating apparatus.

A touch sensitive display, called as a touch screen, may be used as the display unit 706. In this situation, a touch input may be performed via the touch sensitive display.

The above configurations should be considered in descriptive sense only and not for the purpose of limitation, and those skilled in the art will understand that various changes may be made therein without departing from the scope of the present disclosure. For example, although separate units are provided for respective functions of the control unit 701, the control unit 701 may be configured to also perform all or some of the respective functions on behalf of such separate units.

Also, the apparatus may be an electronic device such as, for example, a laptop, a smart phone, a net book, a mobile internet device, an ultra mobile PC, a tablet personal computer, a mobile telecommunication terminal, PDA having a camera and the like herein, just to name some of the possibilities.

It will be appreciated that embodiments of the present invention can be realized in the form of hardware, software or a combination of hardware and software. Any such software may be stored in the form of volatile or non-volatile storage. Also, program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

While the disclosure has been shown and described with reference to certain exemplary embodiments thereof, it will be understood by those skilled in the art that various changes in form and details may be made therein without departing from the spirit and scope of the disclosure as defined by the appended claims. Therefore, the scope of the disclosure is defined not by the detailed description of the disclosure but by the appended claims, and all differences within the scope will be construed as being included in the present disclosure.

What is claimed is:

1. A method for calculating an energy consumption as a function of three-dimensional (3D) motion tracking, comprising:

obtaining a weight and a height of a body comprising a plurality of body segments, each body segment connected with a reference point;

obtaining volumetric weights of each body segment as a function of a body segment factor, a weight factor, and a height factor;

selecting at least one body segment of the plurality of body segments as an analysis target;

calculating a motion quantity of the analysis target as a function of each volumetric weight of the selected at least one body segment by an amount of a movement of a respective reference point of the analysis target using a 3D vector to analyze the reference point; and determining an energy consumption of the analysis target on a basis of the motion quantity, wherein the weight factor is calculated as a function of a first variable of the body segment and the weight, and wherein the height factor is calculated as a function of a second variable of the body segment and the height.

2. The method of claim 1, wherein the reference point includes at least one joint of a body region of the analysis target.

3. The method of claim 1, wherein the 3D vector is acquired by a method of structured light coding or a method of pulsed time of flight.

4. The method of claim 1, wherein the movement of the respective reference point of the analysis target includes at least one of a moving distance and a rotation angle.

5. The method of claim 1, further comprising:

determining a moving speed of the analysis target on the basis of the reference point.

6. The method of claim 1, wherein the energy consumption of the analysis target is determined by 3D optic module technology.

7. An apparatus for calculating an energy consumption as a function of three-dimensional (3D) motion tracking, comprising a processor configured to:

obtain a weight and a height of a body comprising a plurality of body segments, each body segment connected with a reference point;

obtain volumetric weights of each body segment as a function of a body segment factor, a weight factor, and a height factor;

select at least one body segment of the plurality of body segments as an analysis target;

track a trajectory of the reference point before and after a lapse of a predetermined time;

calculate a motion quantity of the analysis target as a function of each volumetric weight of the selected at least one body segment by an amount of a movement of a respective reference point of the analysis target using a 3D vector to analyze the reference point; and determine an energy consumption of the analysis target on a basis of the reference point, wherein the weight factor is calculated as a function of a first variable of the body segment and the weight, and wherein the height factor is calculated as a function of a second variable of the body segment and the height.

8. The apparatus of claim 7, wherein the reference point includes at least one joint of a body region of the analysis target.

9. The apparatus of claim 7, wherein the processor is configured to compare and analyze the reference point before the motion of the analysis target and the reference point after the lapse of a predetermined time using a 3D vector.

10. The apparatus of claim 9, wherein the movement of the respective reference point of the analysis target includes at least one of a moving distance and a rotation angle.

11. The apparatus of claim 7, wherein the processor is configured to determine a speed and distance of the analysis target on the basis of the reference point.

12. The apparatus of claim 7, wherein the processor is configured to use 3D optic module technology, and the apparatus further comprises:

a 3D optic module configured to recognize an object in a 3D manner; and a storage unit configured to store calorie accumulation information calculated in real time.

13. A system for calculating an energy consumption as a function of three-dimensional (3D) motion tracking, comprising:

a processor configured to:

obtain a weight and a height of a body comprising a plurality of body segments, each body segment connected with a reference point;

obtain volumetric weights of each body segment as a function of a body segment factor, a weight factor, and a height factor;

select at least one body segment of the plurality of body segments as an analysis target, and analyze the reference point before and after a lapse of a predetermined time;

calculate a motion quantity of the analysis target as a function of each volumetric weight of the selected at least one body segment by an amount of a movement of a respective reference point of the analysis target using a 3D vector; and determine an energy consumption of the analysis target on a basis of the motion quantity; and a 3D optic sensor configured to recognize the analysis target in a 3D manner, wherein the weight factor is calculated as a function of a first variable of the body segment and the weight, and wherein the height factor is calculated as a function of a second variable of the body segment and the height.

14. The system of claim 13, wherein the reference point includes at least one joint of a body region of the analysis target.

15. The system of claim 13, wherein the processor is configured to compare and analyze the reference point before the motion of the analysis target and after the lapse of the predetermined time using a 3D vector.

16. The system of claim 15, wherein the movement of the respective reference point of the analysis target includes at least one of a moving distance and a rotation angle.

17. The system of claim 13, wherein the processor is configured to determine the speed and distance information of the analysis target on the basis of the reference point.

18. The system of claim 13, wherein the processor is configured to use 3D optic module technology.

19. The system of claim 13, the system further comprising:

a storage unit configured to store calorie accumulation information calculated in real time.

20. The system of claim 13, wherein the processor comprises a control unit of the system.

* * * * *